United States Patent
Chakrabarti et al.

(10) Patent No.: US 11,191,496 B2
(45) Date of Patent: Dec. 7, 2021

(54) SCATTERED X-RAY DETECTION TO DETECT MISUSE AND PREVENT HARM

(71) Applicant: KONINKLIJKE PHILIPS N.V., Eindhoven (NL)

(72) Inventors: Biswaroop Chakrabarti, Kolkata (IN); Prasad Raghotham Venkat, Bangalore (IN); Ravindra Bhat, Eindhoven (NL); Gereon Vogtmeier, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 29 days.

(21) Appl. No.: 16/623,488

(22) PCT Filed: Jun. 26, 2018

(86) PCT No.: PCT/EP2018/067053
§ 371 (c)(1),
(2) Date: Dec. 17, 2019

(87) PCT Pub. No.: WO2019/002257
PCT Pub. Date: Jan. 3, 2019

(65) Prior Publication Data
US 2020/0187877 A1 Jun. 18, 2020

(30) Foreign Application Priority Data
Jun. 27, 2017 (EP) .................... 17178015

(51) Int. Cl.
*A61B 6/10* (2006.01)
*A61B 6/00* (2006.01)
*G21K 1/02* (2006.01)

(52) U.S. Cl.
CPC ............ *A61B 6/107* (2013.01); *A61B 6/4291* (2013.01); *A61B 6/483* (2013.01); *A61B 6/542* (2013.01);
(Continued)

(58) Field of Classification Search
CPC ....... A61B 6/107; A61B 6/4291; A61B 6/483; A61B 6/542; A61B 6/545; A61B 6/548;
(Continued)

(56) References Cited

U.S. PATENT DOCUMENTS

| | | | |
|---|---|---|---|
| 2005/0226382 A1* | 10/2005 | Eck | A61B 6/583 378/117 |
| 2008/0122441 A1* | 5/2008 | Hayakawa | G01R 33/28 324/318 |

(Continued)

FOREIGN PATENT DOCUMENTS

| | | |
|---|---|---|
| DE | 102011005750 A1 | 9/2012 |
| EP | 2982415 A1 | 2/2016 |

OTHER PUBLICATIONS

PCT International Search Report, International application No. PCT/EP2018/067053, dated Oct. 25, 2018.
(Continued)

*Primary Examiner* — David P Porta
*Assistant Examiner* — Gisselle M Gutierrez
(74) *Attorney, Agent, or Firm* — Larry Liberchuk (57) ABSTRACT

An apparatus and related method for supporting X-ray imaging. The apparatus comprises an input interface (IN) for receiving an X-radiation scatter measurement obtained by an X-ray sensor ($SX_i$) during operation of an X-ray imager (XI) for imaging a first object (PAT). A predictor component (PC) is configured to predict, based on said measurement, whether or not: i) a second object (P) is present, or ii) there is sufficient X-ray exposure of said first object (PAT). The apparatus comprises an output interface (OUT) for outputting a predictor signal indicative of an outcome of said prediction.

13 Claims, 4 Drawing Sheets

(52) U.S. Cl.
CPC .............. *A61B 6/545* (2013.01); *A61B 6/548* (2013.01); *A61B 6/563* (2013.01); *A61B 6/583* (2013.01); *G21K 1/025* (2013.01)

(58) Field of Classification Search
CPC ......... A61B 6/563; A61B 6/583; A61B 6/586; A61B 6/587; A61B 6/06; A61B 6/582; A61B 6/4405; G21K 1/025
USPC .......................................................... 378/62
See application file for complete search history.

(56) References Cited

U.S. PATENT DOCUMENTS

| | | | |
|---|---|---|---|
| 2010/0123083 A1* | 5/2010 | Petrick | A61B 6/4233 250/370.09 |
| 2010/0127859 A1 | 5/2010 | Hohmann | |
| 2011/0110573 A1 | 5/2011 | Wiegert | |
| 2012/0170708 A1 | 7/2012 | Tsubota | |
| 2013/0223588 A1 | 8/2013 | Kurochi | |
| 2015/0250435 A1 | 9/2015 | Hyde | |
| 2016/0029980 A1 | 2/2016 | Osherov | |
| 2016/0106384 A1* | 4/2016 | Park | A61B 6/4411 378/98.2 |
| 2016/0106385 A1* | 4/2016 | Park | A61B 6/4494 378/98 |
| 2019/0167217 A1* | 6/2019 | Park | A61B 6/4283 |
| 2020/0178917 A1* | 6/2020 | Park | A61B 6/461 |
| 2020/0367848 A1* | 11/2020 | Okumura | A61B 6/54 |

OTHER PUBLICATIONS

Vano E. et al: "Occupational Dosimetry in Real Time. Benefits for Interventional Radiology", Radiation Measurements, Elsevier, Amsterdam, NL, vol. 46, No. 11, Apr. 26, 2011, pp. 1262-1265, XP028329852.

* cited by examiner

SCATTERED X-RAY DETECTION TO DETECT MISUSE AND PREVENT HARM

FIELD OF THE INVENTION

The invention relates to an apparatus for supporting X-ray imaging, to an imaging system, to a grid structure, to a method of supporting X-ray imaging, to a computer program element, and to a computer readable medium.

BACKGROUND OF THE INVENTION

With wide deployment of DXR (diagnostic X-ray) systems, especially in high throughput centers as well as in centers managed by less qualified personnel, hazardous situations may emerge where people other than the patient may be exposed to X-ray radiation if the system is operated in the presence of unwarranted people in unsafe proximity. This situation may result from a lack of awareness of the user, or from stressful situations in a crowded hospital or through unauthorized/unscrupulous usage. Other incorrect usages of X-ray system may also be observed in these settings.

SUMMARY OF THE INVENTION

There may therefore be a need for solutions that improve usage safety of X-ray imaging systems.

The object of the present invention is solved by the subject matter of the independent claims where further embodiments are incorporated in the dependent claims. It should be noted that the following described aspect of the invention equally applies to the imaging processing system, to the grid structure, to the method of supporting X-ray imaging, to the computer program element and to the computer readable medium.

According to a first aspect of the invention there is provided an apparatus for supporting X-ray imaging, comprising:

an input interface for receiving an X-radiation scatter measurement obtained by at least one X-ray sensor during operation of an X-ray imager for imaging a first object;

a predictor component configured to predict, based on said measurement, whether or not:

i) a second, not imaged, object is present, wherein the at least one X-ray sensor is arranged away from the second object, or ii) there is at least sufficient X-ray exposure of said first object; and an output interface for outputting a predictor signal indicative of an outcome of said prediction.

The proposed apparatus uses the information in the scatter radiation to increase operational safety of X-ray imaging. Scattered X-radiation, usually considered a nuisance, is put to good use with the proposed system to enhance safety. A risk for misuse is reduced and even less qualified personnel may be allowed to perform X-ray imaging. But even experienced staff more often than not required to working long hours in ever busy medical facilities may benefit from the proposed safety features. In embodiments of feature i), the scatter measurements are processed by the predictor component to derive the predictor signal as the second object is approaching the one or more of the sensors.

According to one embodiment, the apparatus further comprising a transducer configured to issue an alert signal in response to the predictor signal, said transducer being any one or a combination of i) auditory or ii) optical. This allows quickly alerting user and others that the X-ray imager is incorrectly used.

According to one embodiment, the apparatus comprises a renderer configured to effect displaying on a display unit a message in relation to the predictor signal.

According to one embodiment, the apparatus comprises a communication component configured to forward a message in relation to said predictor signal over a communication network to a recipient, such a mobile device, remote computer etc. of an experienced member of staff.

The messages in both embodiments may include log files of the imager, details of an imaging protocol and other documentation. The message displayed on the display unit may include information on the nature of the misuse and/or guidance on what should be done to revert to a safe situation.

According to one embodiment, the apparatus comprises a safety enforcer configured to cause an action to at least affect the amount of X-radiation received at the first object, based on the predictor signal. Actions envisaged herein include switching off the imager or at least disable its X-ray source, or collimating primary beam down to an intended region of interest and/or reducing intensity of radiation to an amount still allowed according to imaging protocol.

According to one embodiment, the apparatus the X-ray imaging apparatus comprises an X-ray detector for imaging the first object, and where the at least one sensor is different from said X-ray detector. This allows arranging the sensors (each having preferably a smaller field of view than the detector) in numerous spatial layouts to reliably capture intensity changes of the scattered radiation.

Alternatively, and according to one embodiment, the at least one sensor is part of the X-ray detector. More particularly, the one or more sensors comprise one or more pixels of the X-ray detector. This embodiment may be realized by a grating structure as will be explained in more detail below. This embodiment allows reducing parts count and easier deployment as the mounting of the sensor can be dispensed with.

According to one embodiment, operation of the predictor component is based on a machine learning algorithm trained by one or more samples of X-radiation scatter measurements. Neural networks or other machine learning techniques can be used to enhance reliability and robustness of the predictions.

Alternatively, the predictor component is configured to compare said one or more measurements against one or more pre-defined X-radiation scatter thresholds. If a plurality of sensors is used, the collection of thresholds form a spatial distribution of an expected scatter profile, that is, a position dependent intensity map with locally defined maximum values for the allowed dose.

In either embodiment, test/calibration objects ("(imaging) phantoms") may be used to acquire the samples.

According to a second aspect of the invention there is provided an imaging system, comprising: an apparatus of any one of the above mention embodiment, the X-ray imager and the at least one X-ray sensor.

As mentioned earlier, the at least one X-ray sensor for scatter measurement is arranged remote or away from the second object, in particular is not attached to the second object. Specifically, and according to one embodiment, the X-ray imager resides in a room with the at least one X-ray sensor arranged on a wall or a floor of said room. In addition or instead, the at least one X-ray sensor is arranged on the X-ray imager, such as on X-ray tube housing, gantry, examination table or on other room fixtures or infrastructure.

According to a third aspect of the invention there is provided a grid structure for X-ray imaging mountable on an X-ray detector, comprising a first plurality of walls focused on a first location outside said structure and a second plurality of walls focused on second location outside said structure and different from said first location.

This grid element allows using a subset of detector pixels of the imager itself as the above mentioned sensors. The first location is preferably that of the focal spot of the X-ray source whilst the second location (of which there are preferably more than one) is any other location in space suitable for scatter radiation detection.

According to a fourth aspect of the invention there is provided an imaging system, comprising:
an apparatus of any one of previous embodiments;
the X-ray imager having the grid structure mounted on an X-ray detector of said imager; and wherein at least one X-ray sensor is formed from one or more pixels of said X-ray detector.

According to a fifth aspect of the invention there is provided a method of supporting X-ray imaging, comprising the steps of:
receiving an X-radiation scatter measurement obtained by at least one X-ray sensor during operation of an X-ray source of an X-ray imager to expose a first object to X-radiation for imaging;
predicting, based on said measurement, whether or not:
i) a second, not imaged, object is present, wherein the at least one X-ray sensor is arranged away from the second object, or
ii) there is sufficient X-ray exposure of said first object; and
outputting a predictor signal indicative of an outcome of said prediction.

According to one embodiment, the method further comprises: issuing an alert signal in response to the predictor signal, said transducer being any one or a combination of i) audio or ii) optical.

According to one embodiment, the method further comprises: effect displaying on a display unit a message in relation to the predictor signal.

According to one embodiment, the method further comprises: transmitting a message in relation to said predictor signal over a communication network to a recipient.

According to one embodiment, the method further comprises: causing an action to at least affect the amount of X-radiation received at the first object, based on the predictor signal. Said action may include any one or a combination of: shutting down or locking down the imager, in particular the X-ray source of the imager, re-collimating, reducing voltage in the X-ray source of the imager. Other or additional actions may include changing X-ray source amperage and/or changing exposure time and/or mode (eg, pulsed or continuous). Said actions may be performed in a pre-defined sequence or in "cascaded" fashion, on after the other until safety is restored. In particular it may not be necessary to perform all actions in the sequence.

According to a sixth aspect of the invention there is provided a computer program element, which, when being executed by at least one processing unit, is adapted to perform the method.

According to a seventh aspect of the invention there is provided a computer readable medium having stored thereon the program element.

"X-ray exposure" relates to manners in which the X-radiation is allows to impact on the patient. The exposure relates to the dose received or receivable by the patient and is a function in particular of an X-ray source setting (voltage, amperage and or time).

"Sufficiency of exposure" is a function of an agreed image quality and body mass of the patient. Image quality (eg, contrast), and hence sufficiency of exposure can be quantified by a number of different metrics, including SNR (signal-to-noise ratio) and others. The dose should be as low as possible to still achieve the (pre-set) image quality.

"Imaging" as used herein includes in particular exposing at least a part of the patient with X-radiation from the X-ray source of the imager for the purpose of acquiring an image of at least the part of the patient for diagnostic or other medical purposes. This type of imaging or X-ray exposure may also be referred to herein as "actual imaging". However the term "imaging" as used herein may also be include "preparatory imaging", sometimes called "scout imaging", where the X-ray exposure is performed at a lower voltage setting and/or lower amperage and/or lower exposure time than for the actual imaging, for instance in order to check proper positioning of the patient. After scout imaging, the actual imaging at a higher tube voltage or amperage or exposure time commences.

"first/second objects" refer in particular to animal or human patients, bystanders, or people in general, as medical applications are mainly envisaged herein. However other imaging applications in relation to in-animate objects are not as such excluded herein, for instance when inanimate objects are involved that may be destroyed by exposure to X-ray. In particular in the medical context mainly envisaged herein, the first object is a patient to be imaged and the second object is an additional person.

"Radiation" or "scatter" should be interpreted herein as references to X-radiation and scattered X-ray radiation, respectively.

"X-radiation" is shorthand for X-ray radiation.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
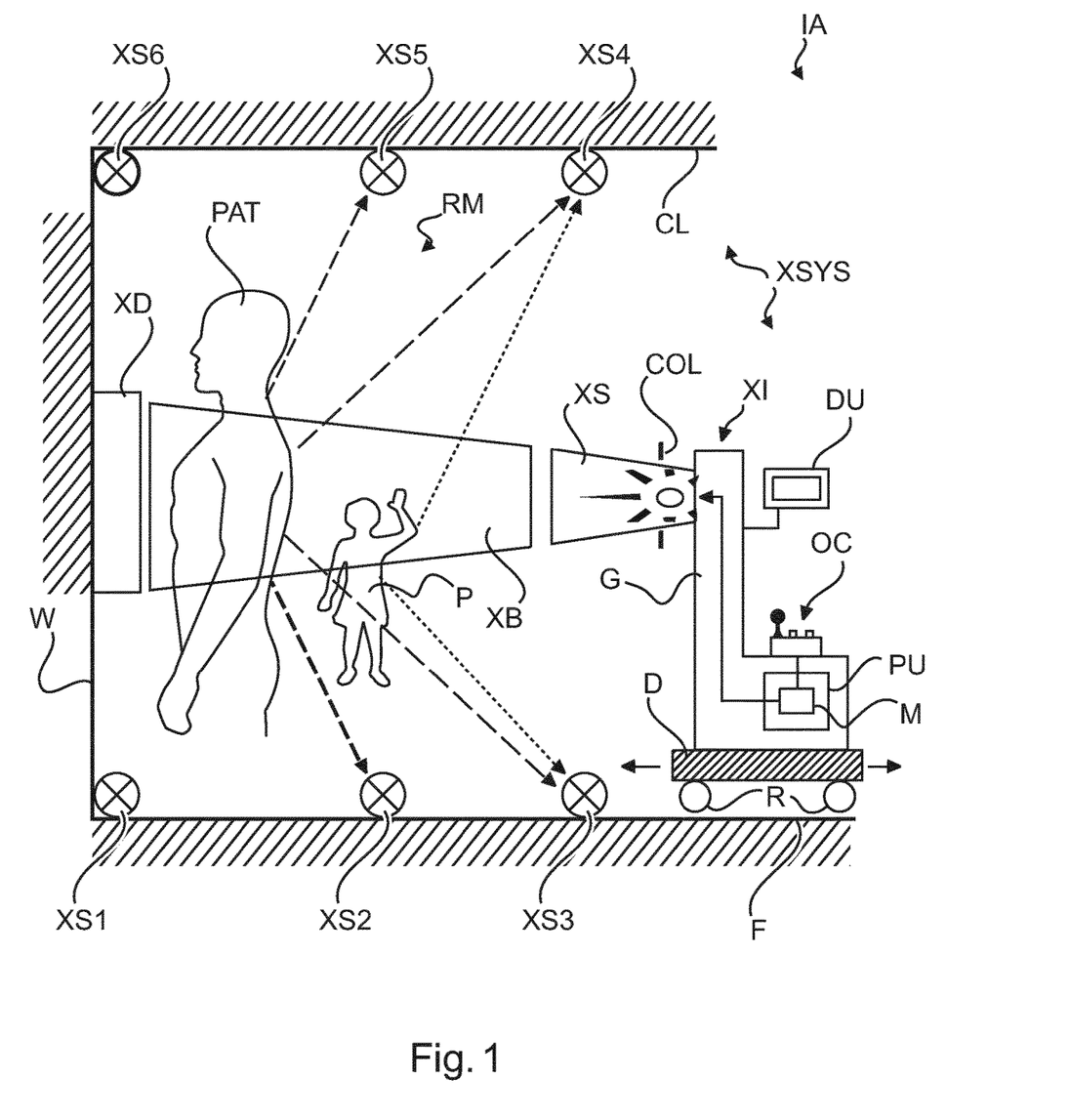
FIG. 1 shows a schematic block diagram of an imaging system.

With reference to FIG. 1, there is shown an imaging arrangement IA. The arrangement includes an X-ray imaging apparatus XI (also referred to herein as the "(X-ray) imager") and a system XSYS comprising safety module M (referred to herein as "the module") that supports safe operation of the X-ray imager in a manner to be described in more detail below.

The X-ray imager XI as mainly envisaged herein is of the mobile or portable type. One such embodiment of a mobile X-ray imager XI is shown schematically on the bottom right of FIG. 1.

The X-ray imager XI is mobile or portable in the sense that it can be moved from one location, such as from an examination room RM, to another location, in particular to another examination room. This is particularly useful in settings where it is impractical to have a dedicated examination room. The imaging can advantageously be performed in any room that happens to be vacant at a given time. Preferably, there is no disassembling required when moving the mobile imager XI to the other usage location. The mobile X-ray imager IA as envisaged herein in one embodiment includes a dolly D or undercarriage with rollers R. Erected on said moveable undercarriage is a gantry G that holds the X-ray source XS.

The X-ray imager further includes an X-ray sensitive detector XD, preferably of the digital type, in particular in flat-panel technology. The X-ray tube XS is arranged preferably moveably on the gantry G so that tube XS can be aligned with the X-ray detector XD. Alternatively, the source XS is fixed and the detector XD is movable on a fixture for alignment with the X-ray source XS.

In the mobile embodiment shown in FIG. 1, there is no physical or structural connection between the X-ray detector XD and the remainder of the X-ray imaging apparatus. In particular, the X-ray detector XD is not mounted on an arm of the gantry although this may still be so in other, alternative embodiments. More compact, portable, solutions as the one shown in FIG. 1 are also envisaged in alternative embodiments, for instance for use in ambulance vehicles. In these portable embodiments, the X-ray imager XI may not necessarily include rollers R but is compact and light enough to be carried (possibly in a suitable carrying case) from the ambulance to the incident site. The X-ray source XS and/or the detector XD of the imager XI may be releasably mountable in suitable fixtures arranged inside the vehicles, e.g. on the vehicle's cabin wall for instance. "Vehicles" as envisaged herein include not only land travelling vehicles (cars, vans, etc.) but also aircraft (helicopters, airplanes) or ships. Although mobile or portable imaging systems are mainly envisaged herein, this is not at the exclusion of other traditional, fixed settings such as C- or U-arm X-ray imager or CT scanners. The X-ray imager XI may be powered by an external power supply through a power cord connected to a power output, or the imager XI may have an autonomous on-board energy source such as batteries.

The X-ray imager XI further includes an operator console OC that allows the user to perform various control functions such as configuring various imaging settings or parameters and starting X-ray exposure for imaging. The operator console OC is implemented as functionalities of an on-board computing unit PU. Alternative embodiments are also envisaged where the computing unit PU is outsourced to remote server system, communicatively coupled to the imager XI.

The configurable imaging settings include in particular the X-ray source ("tube") settings which include the voltage at which the X-ray source is to be operated for an imaging session. Other X-ray source settings include the energy of the X-radiation so produced, specifiable in keV and/or the duration of exposure and/or the frequency of the exposure, and other parameters such as tube amperage. Other imaging settings include the imaging geometry. The imaging geometry relates to the mutual geometrical configuration of the patient PAT relative to source and detector. The imaging geometry also includes the "SID" distance (distance between source XS and detector XD). The imaging settings may be configured by a suitable user interface UI (textual or graphical) of the operator console OC.

The user can further input, by said user interface UI or a different user interface, patient characteristics, in particular sex, height, weight, age, patient ID (identification information (e.g. patient number) that allows establishing the specific identity of the patent PAT to be imaged, etc.

The user may select some or all the imaging settings directly or indirectly by choosing an imaging protocol that prescribes appropriate, and in most cases mandatory, imaging settings that match the patient characteristics.

In other words, the imaging settings as per the image protocol are in general a function of i) the patient characteristics and the imaging task to be performed on the patient PAT. The imaging task defines the purpose of the imaging, in particular the organ or body part to be imaged. The imaging protocol ensures a certain image quality and is designed to ensure the patient dose/exposure is as low as possible. The exemplary embodiment in FIG. 1, shows a set up for a lung or chest imaging procedure. In this particular example, the patient PAT is required to stand whilst in other imaging situation patient PAT lies on an examination table (not shown) arranged between X-ray source XS and detector XD.

Instead of adjusting manually some or all of the patient characteristics and/or the imaging setting or instead of selecting manually the imaging protocol by the user through the UI as described above, the patient characteristics and/or the imaging setting and/or the imaging protocol may be adjusted or selected automatically, e.g. through the computing unit PU by retrieving patient data through a network (not shown) from a data source (e.g., electronic health record) and then matching same to data in a medical knowledge database DB to find the appropriate imaging settings/imaging protocol. The imaging protocol is preferably specified in a machine readable format, such as XML, DICOM or other.

The X-ray source XS includes in general an evacuated tube. Inside the tubes there are arranged an anode and a cathode. The cathode is usually a rotating disc. When power is applied across the anode and the cathode, electrons are emitted from the cathode and accelerated from the cathode towards the anode. Upon impact of the election beam at a focal spot on the cathode disc, X-radiation is produced which exits the X-ray housing of the X-ray source through an exit window towards the patient PAT and the X-ray detector XD. In other words, the patient PAT or the body or organ of interest is arranged in a space between the X-ray source XS in particular at its focal spot and the detector XD. Yet more particularly, the electron beam emitted from the cathode impacts the rotating anode disc at a focal spot from which the X-radiation is emitted towards the patient PAT.

The X-radiation so generated exits the X-ray housing in form of a primary beam XB which may be suitably collimated by a collimator COL. The collimated X-ray beam is usually of cone, pyramidal or fan shape, depending on the imaging technology used. The collimator allows adjusting a width of the primary X-ray beam. In particular, the collimator can decrease the cross-section of the beam XB. Collimator settings may be user adjustable through the operator console OC and/or may form further imaging settings prescribed in the imaging protocol.

The primary X-ray beam XB is formed from streams of photons, and the volume flooded by said primary X-ray beam corresponds to all trajectories along which photons can ideally travel. When there is no patient PAT in the beam, these trajectories are straight geometric lines that extend from the focal spot to different pixel positions of the detector XD. However, when patient PAT resides between X-ray source XS and detector XD, photons travel through tissue. The photons then interact with patient tissue of, in general, different type and density (bone, fat, muscle, etc.). This interaction includes in particular attenuation. In other words, the intensity with which the photons are registered by radiation sensitive pixels PX of the detector XD at the far end of the patient is decreased, compared to the intensity the photons had prior to impacting the tissue. The intensity variations detected at the detector, at least partially, correlate with structural features, in particular density of the tissue. In other words, the structural density variations are modulated onto the intensity variations and this confers image contrast. The detected intensity variations can then be used to form digital images of internal anatomy of the patient. Specifically, photons that impinge on the detector surface after travelling through the patient cause, according to their intensity, an electric signal at respective pixels. These electrical signals ("raw data") are then together processed by a suitable AD-conversion unit into digital image signals. The digital imaging signals are transmitted via a wired or wireless connection communication network to the processing unit PU where imaging processing software is run and where the images are then produced. The images can then be displayed on a display unit DU. The display unit DU is preferably part of the X-ray imager XI but this may not be so necessarily in all embodiments. The displaying of the images may be affected in real time. Instead of, or in addition to, displaying the images, these may are transferred via wired or wireless communication network into storage for further processing or later review.

Referring back to the physical process of intensity attenuation of the X-radiation, this physical effect is twofold. For one, the intensity attenuation is a result of the photons being at least partly absorbed in the tissue. However, another reason why there is attenuation is that some of the photons are scattered. Scattered x-radiation is indicated by dashed arrows in FIG. 1. When undisturbed by intervening objects/tissue, the photons would travel along ideal trajectories which are straight lines from the focal spot through the patient and onto a certain target pixel. But when in particular patient PAT is situated in the photon's trajectory, some photons are scattered after interaction with patient tissue. Said differently, the photons are veered off their ideal straight trajectory into other trajectories in a multitude of different directions, including across the main direction of the primary beam XB. Instead of being absorbed by patient tissue PAT or instead of impinging on a detector pixel the scattered photons interact with other objects in the exam room RM, in particular with one or more persons P that happen to be in the room during X-ray exposure of patent PAT.

Useful as X-radiation may be for X-ray imaging, it has also negative side effects and can cause serious health risks. Unnecessary exposure of humans or animals to X-radiation, in particular with scatter x-radiation, should be avoided. It is then proposed herein to foster safer operation of the X-ray imager XI by providing a system XSYS. The system includes a data processing safety module M (referred to herein as "the module") that processes the scattered radiation to establish in one embodiment whether or not there is another person P in the exam room during imaging.

The principle of operation of the module M is that when at least one additional person P is present in the examination room (in sufficient proximity to the X-ray source XS), this additional person P (who is not imaged) will themselves produce scatter radiation when the radiation scattered off the patient PAT interacts with that additional person P. This additional scatter is indicated in FIG. 1 by dotted arrows. The proposed safety support system XSYS includes one or more sensors $XS_i$ that allow detecting this additional scatter which is above the normal scatter to be expected (see the dashed arrows) if there was no additional person P in the examination room other than the patient PAT.

In addition or instead of this person presence detection by means of scatter, the safety module SM may operate to predict whether the patient PAT has actually received the correct dose of X-ray exposure. "Correct dose" means in particular an X-ray source setting that ensures low (or lowest possible) dose for the patient whilst delivering an agreed image quality. Again, the information included in the scatter radiation is used to this end. More particularly, the patient PAT having a known mass will produce a known amount of scatter (shown in dashed arrows). If not enough scatter is generated, this may indicate that the voltage or energy keV at which the tube is currently operating is not sufficient or that the exposure time of the patient was not long enough.

Various embodiments for the safety module M and for the supporting sensors $XS_i$ are envisaged. One such embodiment is shown in FIG. 1 where the six dedicated X-radiation sensitive sensors XS1-XS6 are distributed suitably in the examination room RM. In this or similar arrangements, some of the sensors XS1-XS3 are arranged on the floor or are integrated into the floor of the examination room RM and/or one or more other sensors XS4-XS6 are integrated or attached to the ceiling CL of the examination room RM.

In particular, the one or more sensors XSI are arranged outside the volume of the primary X-radiation beam XB. For instance, instead of in addition to a wall W or ceiling Cl or floor FL mounted sensor arrangement, one or more of the sensors XI may be arranged on the gantry G, e.g. on the X-ray housing XS outside the exit window of the X-ray housing or on any other parts of the imager XI itself. Although FIG. 1 shows six such sensors, this is an exemplary embodiment, and in principle fewer or more sensors [collectively referred to herein in indexed notation as "XSi" (with index i an integer I≥1)] could be used. A single such sensor XS1 may be sufficient in some applications. It may be advantageous however to arrange a plurality of such sensors $XS_i$ in a symmetrical manner around the X-ray source XS but outside the volume of the beam XB to better pick up the scatter X-radiation.

The underlying technology of the scatter sensors XSi may be the same as that of the primary X-ray detector XD. In other words, all existing direct and indirect conversion technologies can be used. However, it is envisaged herein that the sensors are cheaper and have a much smaller field of view than the imaging detector XD. Specifically each or some of the sensors may be arranged as a single pixel detector as this may be sufficient to pick up a scatter signal. A field of view of a group of a few pixels (eg about 5×5 pixels or 10×10 pixels or other) is also envisaged, with the size of the sensors XSi about that of a coin or similar, eg, a few centimeters across. The field of views of these sensors can be of any convenient shape, such as rectangular (eg, square) or round.

Arranging the sensors XSi in a distributed fashion (as shown in FIG. 1) as physically separate and discrete from the X-ray detector XD is a preferred embodiment, but alternative embodiments are also envisaged where it is the detector XD itself that is used for measurement of the scatter radiation (this alternative embodiment will be described in further detail below at FIG. 3).

Figure 2:
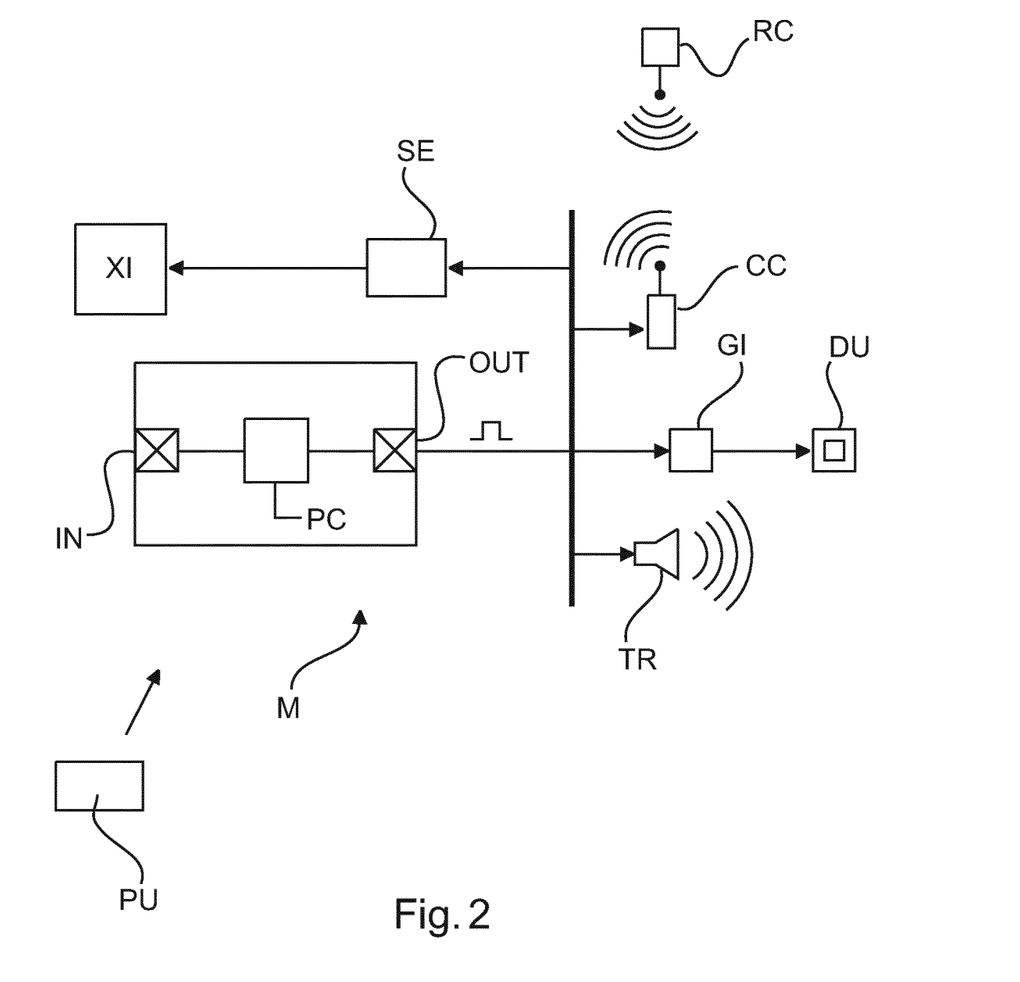
FIG. 2 shows a more detailed block diagram of a module used in the imaging system in FIG. 1.

Turning now first in more detail to the operation of the safety module M, this is shown as a block diagram in FIG. 2. The module M comprises an input port IN and an output port OUT. The module includes a predictor component PC. Scattered radiation is measured at one or more sensors $SX_i$ or, in an alternative embodiment, by the detector XD itself. The measurements are received at input port IN. The measurement signals are then processed by the predictor component to produce a signal ("predictor information signal") at output port OUT that indicates whether or not the (at least one) additional person P is present in the examination room during imaging, or whether patient PAT has received sufficient X-ray exposure. More particularly and according to one embodiment, the predictor PC may be configured to predict whether the used X-ray tube setting is optimal for the given body mass of the patient and a given image quality. It should be noted, although body mass as one of the main factors to be considered, mass distribution may also be a factor for consideration. For instance, although a patient with high body mass may still have normal proportions at certain regions of interest. It may then be not necessary to use a higher tube voltage when imaging said regions of interest.

This predictor information signal can then be processed in different ways all of which are envisaged herein in different embodiments, singly or in combination. For instance, in one embodiment the signal is used to drive a transducer TR such as a flashlight or a loudspeaker to indicate the presence of the person P. In addition or instead, the transducer may indicate that the patient PAT is not receiving the required X-ray exposure as would be required by the patient's characteristic (in particular body mass) and the imaging protocol. In addition or instead, the prediction signal may be used to instruct renderer GI to render graphically or in text form on display unit DU an indication on the X-ray energy keV that should be used instead. In other words, the prediction signal is used to encourage the user to correct usage.

In one embodiment there is also a safety enforcer SE which uses the information signal produced by the predictor component PC to initiate action to prevent incorrect usage of the X-ray imager. This action may include shutting down the X-ray imager XI or pass at least the X-ray source XS into lock-down. Less intrusive actions are also envisaged that will affect (in particular reduce) the amount of radiation received at the patient PAT. For instance, the action initiated by the safety enforcer SE may include operating the collimator COL to decrease beam cross-section. Other actions include moving patient PAT out of the beam XB by actuating actuators of a motorized examination table on which the patient PAT lies during exposure. In general, the safety enforcer SE is configured to process through suitable logic circuitry whether the predictor information signal indicates a violation and. If there is violation the safety enforcer SE issues though middleware components and interfaces suitable hardware commands to effect the desired action. The actions may be performed in one embodiment in a cascading fashion according to their intrusiveness. Only if performing an action of lesser intrusiveness is not capable of restoring safety, an action at a higher intrusiveness is taken. For instance, in a first stage a re-collimation is attempted. If this does not help, the X-ray imager is shut-down or passed into lock-down. In case presence of the additional person PA is established, other actions initiated by the safety enforcer SE include changing the tube settings, in particular lowering the tube voltage (and hence the keV value) and/or the amperage, if the image quality is still acceptable as per the ranges prescribed in the applicable imaging protocol.

In one embodiment the system XSYS includes a communication component or interface CC to transmit a message through a suitable communication network to a receiver component RC. The message may be informed by the predictor information signal. Based on the predictor information signal, the message may include, in particular, an indication that an incorrect use of the imager XI has occurred. In particular, the incorrect usage includes either that presence of the additional person P has been detected by the predictor component PC during exposure or that there is an on-going exposure with incorrect keV setting. The incorrect usage may have occurred because of an inexperienced or overworked user. The receiver component RC may be a hand held device, or a stationary computer, or a server etc. of a supervisor entity. The supervisor may be human such as an experienced health care professional or may be automated. Once the supervisor is notified about the incorrect usage, the supervisor may then ask for suitable action to be taken, e.g. ask the user for a meeting or instruct the security enforcer SE to disable the X-ray imager. Alternatively, the supervisor may judge the usage violation is not severe enough. The supervisor may then instruct the safety enforcer SE to release the imager XI to allow continued usage.

Turning now to operation of the predictor component PC in more detail, various embodiments are envisaged herein.

In the first embodiment and as briefly mentioned above, the predictor component is configured to predict presence of additional person P in the examination room whilst a patient PAT is being exposed to X-radiation. Machine learning techniques, in particular supervised learning techniques, can be used to process a set of previously acquired scatter radiation measurements (also referred to herein as "scatter profile" samples). Using one or more of the sensors $XS_i$, in a calibration phase, samples of scatter radiation profiles are acquired using preferably a range of different phantoms. "Phantoms" are artificial models that include water packages and/or other materials that allow, in approximation, to simulate the behavior of the human body under X-ray exposure. Purely for convenience sake, in the following we will occasionally refer to the phantoms as "patient phantom PAT" or "additional person phantom P" or similar, depending on where the phantom is placed. It is preferable herein to have a range of phantoms each of different mass available to better simulate a population made up of children and adults in various weight ranges. One suitable test range includes imaging phantoms at about 15-20 kg or even less (representing a child), with additional, heavier imaging phantoms increasing in increments of 10 kg up to say 80 or 90 kg. This range of phantoms with different respective mass should cover the range of body masses one usually experiences when imaging human patients. Alternatively, a set of modular phantoms may be used instead, each having a certain mass and the required phantoms are "built" by combining the modular phantoms into combo-phantoms to so realize phantoms with higher masses as required.

This range of phantoms can be used to train a machine learning algorithm, such as neural networks, support vector machines (SVM) or others. The machine learning algorithm is adjusted by learning to distinguish, based on a scatter profile measurement from the phantoms, whether an additional person P is in the examination room during imaging. To do this, the calibration procedure may proceed in two stages. In the first stage, samples of reference scatter profiles are acquired by placing one phantom from the mass range, one at a time and in alteration, into an examination region between the X-ray detector XD and the X-ray source. The X-ray source XS is then operated to expose the phantom to radiation at a given tube keV setting and geometry. This exposure causes a scatter profile which is recorded by the sensors XSi for each phantom, one at a time. In this manner, a set of corresponding scatter measurements is recorded. The scatter so recorded is solely caused by the exposure of respective phantoms in the examination region. To be clear, in this phase of the calibration, no additional phantom is placed in the examination room around the imager. In this manner then a number of different scatter radiation profiles are acquired, one for each of the different imaging phantoms having different masses.

In the second stage of the calibration phase, the imaging phantoms are placed one at a time and one after the other in the examination region between detector and X-ray source as before, but this time an additional phantom is placed in the examination room and again an exposure is performed and the resulting scatter profile is recorded. The scatter profile will increase due to the presence of the additional phantom in the room. The phantom for the additional person is then exchanged for a heavier one and so on, until for each phantom in the range of phantoms for the additional person P, a corresponding scatter profile is recorded. One then proceeds by replacing the patient phantom with one of a larger mass in the range and repeats the respective measurements during exposure for each of the different additional person phantoms P.

At the conclusion of the two calibration phases, one has acquired two sets of "labeled" samples of scatter profiles through X-ray exposure: one set where there were two phantoms present in the examination room: one for the patient and one for the additional person; and another set where no additional phantom P was present other than the patient phantom PAT.

In one exemplary embodiment, a neural network is then set up by defining input notes at which the sample measurements are fed into the network. In this embodiment the output layer of the network can comprise merely two nodes, one node indicating the presence of the additional person whilst the other node indicates that no other person was present. One or more hidden layers can then be defined having two, three or more nodes. The so specified neural network can then be optimized using otherwise known forward/backward-propagation based optimization techniques to adjust the weights of the network to so achieve the training. In this manner the neural network learns the distinguishing signatures of the scatter profiles in respect of the presence or non-presence of the additional person phantom. Once the weights are optimized, the nodes structure can be stored in a memory and is then ready to classify previously unseen scatter profile measurements when deployed in the proposed predictor component PC. Again, this neural network embodiment is exemplary and machine learning techniques other than neural networks are also envisaged herein.

Simpler embodiments are also envisaged herein where no machine learning algorithms are used. For instance in one embodiment a simple thresholding is used to define a set of suitable scatter profile intensity thresholds. These are again obtained in a calibration phase from samples of reference scatter profiles. Later, during use, the scattered radiation profiles as measured at the sensors $XS_i$ are compared against those pre-defined thresholds to conclude whether or not the additional person P was present during the imaging of patient PAT.

In the calibration phase for the thresholding embodiment, again, as in the machine learning embodiment, a range of imaging phantoms with different masses can be used to determine those pre-defined intensity profile thresholds. The calibration procedure for this thresholding embodiment proceeds in the same way as previously described in relation to the machine learning embodiment above. However, in the thresholding embodiment, for each patient phantom PAT, the respective increases in scatter profile intensity is computed by simple subtractions from the respective scatter profiles acquired when the additional person phantoms P were present. The so obtained set of scatter radiation intensity increases can be processed in a number of different ways into the respective intensity thresholds. The set of thresholds is associated with the respective mass of the patient phantom.

For instance, in one embodiment, a simple averaging is performed of all intensity increases for a given patient phantom. In an alternative embodiment the maximum or the minimum increase is used as the respective threshold. The so computed thresholds are then stored in memory accessible by the predictor component PC. Preferably, when the predictor component is in use, the weight of the given patient to be imaged is specified by user input or is otherwise retrieved by the predictor component from a database, such as an electronic health record. The weight information of patient PAT is used to access the associated, expected scatter thresholds. If the weight of the given patient is different from the imaging phantom used for the patient, the associated threshold values can be suitably interpolated by the predictor component PC. Once the "real world" scatter intensities are acquired by the sensors XSi for a real patient PAT during clinical use, this is then compared against the pre-stored or interpolated thresholds. If the measured intensity exceeds the threshold, the predictor component issues the predictor signal that indicates presence of an additional person P during the imaging. If the measured scatter profile does not exceed the threshold, the predictor signal indicates no additional person is present. When more than one sensors XSi are used, the measurement can be collapsed into a single value (as described above in relation to the threshold computation). This can be done by averaging or finding the maximum or minimum. It is then this single value that is compared against the thresholds. A vectorial treatment of all measurements as a whole from all sensors XSi is also envisaged herein in alternative embodiments. In these embodiments it is then also the thresholds that are expressed as vectors, rather than scalar values obtained through averaging etc. as described above. In case of the vectorial treatment, eg $(m_1, \ldots m_i)$, with $m_i$ being the measurement of sensor SXi, the thresholds may be expressed in terms of (squared) Euclidean distance or other suitable metric.

The above described embodiments of the predictor component PC can be refined in a number of different ways. For instance, it has been observed by Applicant that a critical event is not merely whether or not an additional person P is in fact in the examination room during the imaging but, more specifically, whether or not the additional person is within a pre-defined "danger zone" around the imaging apparatus and hence the X-ray source. For instance, one may define a radius of around 50 cm to one about a meter around the pre-defined location for the X-ray source XS in the examination room. The danger zone is hence a spatial subset of the relevant examination room. In the above described embodiments for configuring the predictor component, the additional person phantom P is then positioned somewhere within the danger zone and the thresholds or the machine learning algorithms is then so trained to take into account only the presence within the danger zone. A presence inside the room but outside the danger zone will then be flagged up by the predictor component PC as a non-presence event.

It will be also understood that the previously described calibration phases to acquire the scatter profile data may need to be performed for each of the examination rooms separately, unless the rooms are sufficiently similar with a similar spatial arrangement of the sensors XSi.

The arrangement of the one or more sensors $XS_i$ in the examination room may be done in a multitude of different configurations, so long as the sensors XSi are placed outside the volume traversable by the beam XB of primary radiation. It may however be beneficial to arrange the sensors $XS_i$ in a symmetrical way around the danger zone. This symmetric or uniform arrangement around the danger zone may make it easier to configure the machine learning algorithm to recognize underlying intensity variation pattern. Specification of the patient's weight may also be helpful in the machine learning algorithm, because this information constitutes prior information that again may help the machine algorithm reach the correct conclusion about the presence of the additional person.

In addition to or instead of the above described presence detection capability, the predictor component PC may be configured to establish whether, based on the scatter intensity measurements, the given patient PAT has received sufficient X-ray exposure. Once the mass of the patient is known and given a pre-set image quality, the correct radiation energy keV required from the X-ray tube is pre-determined. It is also expected that a patient PAT will cause more scattered radiation the more body mass he or she has. In other words, the radiation sample measurements may also be used to establish whether the tube is operated at the correct tube setting, in particular voltage for the given patient with given mass to ensure low (eg lowest possible dose) for patient PAT whilst pre-set image quality can be achieved. If the patient PATs mass is known, then too low a measured scatter radiation at sensor $SX_i$ may be taken to indicate that the currently used tube XS setting (eg voltage/keV setting) is too low to achieve the required image quality and needs re-adjusting and this event may be flagged up by the predictor component by issuing a respective predictor signal. This predictor signal indicating under-exposure may then be forwarded to the safety enforcer SE as previously described to initiate suitable action or inform the supervisor entity RC. The relationship between patient mass and expected scatter radiation levels may be learned as described above by machine learning algorithms or by thresholding, both based on sample scatter measurements obtained through use of phantoms as previously described. Again, interpolation may be required to accommodate the specific body mass of patient PAT at hand. The safety actions by enforcer SE may be executed automatically, but preferably is done after approval to the user, for instance by seeking confirmation through displaying an appropriate message on display device. Seeking such an approval is preferably done when an insufficient exposure is detected. An automatic execution of the safety actions without reconfirmation by the user is envisaged however for the case that the presence of another person P is predicted by the predictor to ensure safety.

The proposed safety support system XSYS may be run as suitable software module with suitable interfaces on the computing unit PU onboard the imaging apparatus AI. Alternatively, some or all components may be arranged in hardware such as on a suitably programmed FPGA (field-programmable-gate-array) or as a hardwired IC (integrated circuit) chip. In this sense the system may be integrated into the respective imager XI. Alternatively, one or all functionalities of the proposed system XSYS may be performed in the "cloud", that is, by one or more servers to which the imager XI is communicatively coupled. The functionalities of the system XSYS may be performed centrally by one or more servers to support one or more imaging apparatus XI. The proposed system XSYS including one or more sensors $SX_i$ may be used to retro-fit existing imagers XI.

It should also be understood that the acquisition of the scatter radiation measurements by the one or more sensors XSi and the processing by the proposed predictor component PC of safety module M may be done in a one-off operation during the imaging procedure. Preferably however the measurement acquisitions and the processing by predictor component PS are done in a loop at a reasonable sampling frequency to so implement a dynamic system that can detect dynamically changes during the imaging. For instance, it may well be that initially there is no person in the room so the X-ray exposure of patient PAT can commence. However, at a later stage during the imaging, additional person P then enters the exam room and this situation will then be picked up by the proposed system and acted upon as described above so that any one of the above described actions may be initiated by safety enforcer SE during an ongoing imaging procedure. In other words, by having the predictor component process an incoming stream of updated scatter radiation measurements as acquired by the one or more sensors $XS_i$, a dynamic safety system can be implemented that reacts in essentially real time once the surrounding field of scatter radiation intensities changes due to one or more people entering the examination room.

As briefly mentioned above, rather than having the scatter radiation sensors $XS_i$ arranged as discrete and separate components, different from the main X-ray detector, alternative embodiments are envisaged where one or more part of the main detector XD's pixels are used for picking up the scatter radiation. This detector-sharing embodiment will now be explained in more detail with reference to FIG. 3.

In order to use the imager's XI X-ray detector XD (primarily envisaged for imaging the patient PAT), it must be ensured that certain of its detector pixels px are made to receive only, or at least predominately, scatter radiation rather than primary radiation XB.

Figure 3:
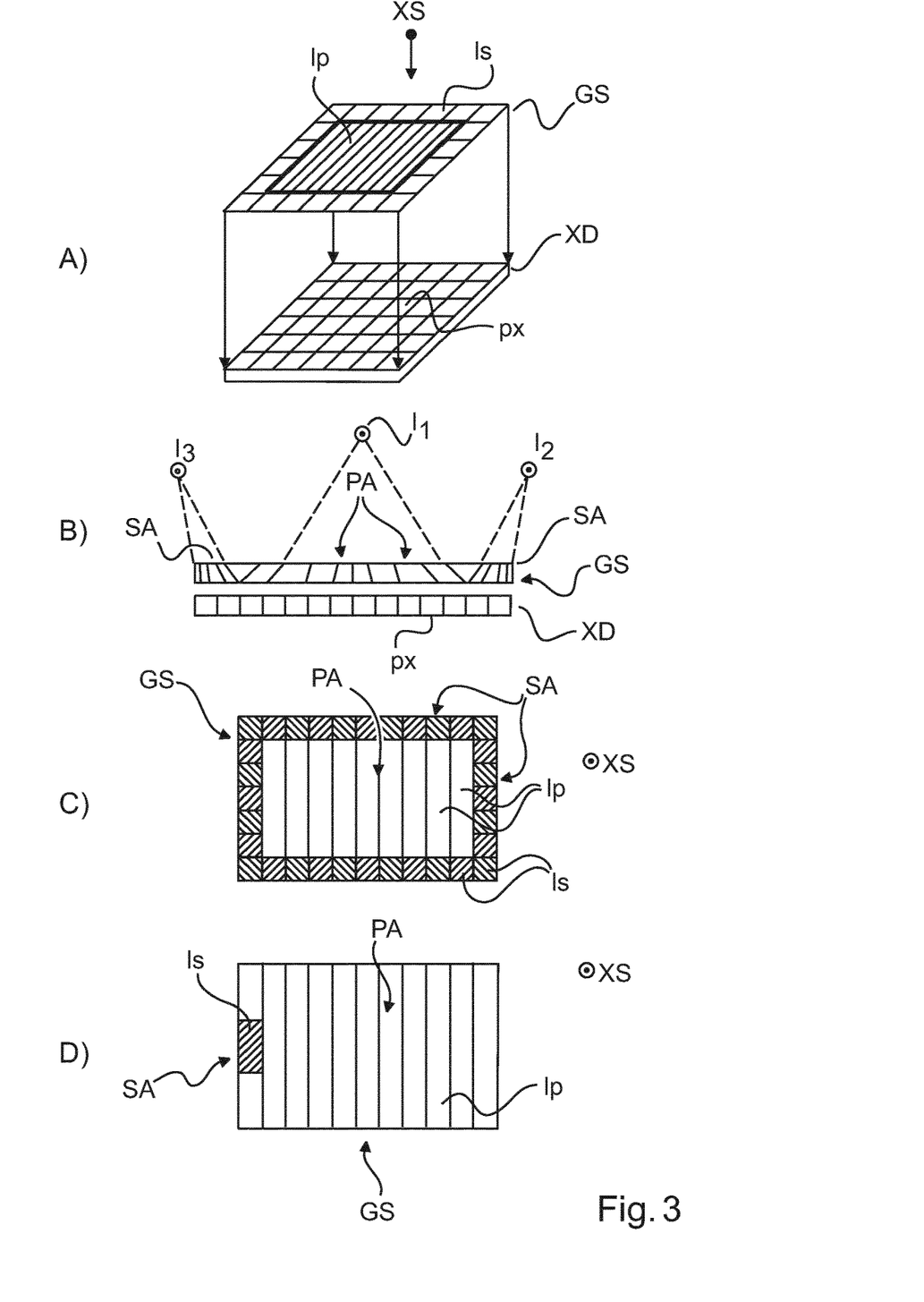
FIG. 3 shows different views and embodiments of a grating structure for an X-ray detector.

One way to do this is shown in FIG. 3 A) in perspective view. A grating structure GS, similar to an anti-scatter grid (ASG), is mounted on top of the detector XD, that is, on top of the radiation sensitive surface formed from the pixels px. In other words the grating structure GS is arranged, when in use, between the X-ray source XS and the radiation sensitive surface of the X-ray detector XD.

The grating structure includes a plurality of strips of "walls" together forming a grid with interspaces between any to neighboring strips lp. The interspaces may be filled with filler material (such as cellulose (paper), a plastic, a foam, etc) that is essentially X-ray transparent. The walls themselves are formed from high density, highly absorbing materials such as tungsten or other. Some of the strips lp are focused in the sense that they are angled (around respective axes parallel to the top view afforded by FIG. 3 A) so that primary radiation as per the primary beam XB can pass essentially unattenuated through the grid stricture GS to impinge underlying pixels px of detector XD. In other words, some of the strips lp are focused on the location $l_1$ (see FIG. 3 B)) in space of the focal spot of the X-ray source XS. However, unlike existing ASGs, whose walls are all so focused on the focal spot, the proposed grating structure differs in that it includes portions SA whose walls are not focused on the focal spot of the X-ray source, but are specifically and deliberately directed away from the focal sport location, preferably in a plurality of different directions towards different locations $l_2, l_3$ (see FIG. 3 B)) in order to pick up scatter radiation instead of primary radiation. Consequently, the top surface of the grid GS structure is made up of two portions: a primary radiation admitting portion PA that admits primary radiation but blocks out scattering radiation and in addition, a scatter radiation admitting portion SA that does admit scatter radiation onto the underlying detector pixel but blocks out primary radiation. Such a grid GS according to one embodiment is shown in side elevation in FIG. 3 B) whilst FIG. 3 c) shows more details in plan view, from top, that is, from the X-ray source/focal spot location along the main propagation direction of the primary beam XB. The shape of the grating structure GS is in general the same as that of the field of view of the detector XD, in this case rectangular. In this embodiment, the scatter radiation admitting portions SA are formed as a border or rim portion around the central primary radiation admitting portion PA of the grate structure GS. The strips is in the scatter admitting portion SA are focused away from the X-ray source to different locations of the examination room, for instance, towards an entrance of the room RM through which the additional person P may enter the room. As shown in plan view in FIG. 3 C) there is scatter admitting portion SA surrounding the primary radiation portion PA. However, other embodiments are also envisaged where the scatter admitting portion SA does not run the whole of the periphery of the grating structure GS. For instance, the scatter admitting portion SA may be arranged in only one, two or three of the four sides of the grating structure. In the embodiment of FIG. 3 D), the scatter admitting portion SA is only arranged on one side of the full field of view. In any case, it is preferable to have the scatter admitting portion SA arranged close to the periphery to minimize disturbance of the main field of view in the primary radiation admitting portion PA. Furthermore it will be understood that for the purposes of scatter radiation pickup, just a very few pixels are required and correspondingly the scatter radiation portion SA of the grid structure may be very small, merely a few pixels wide, so the reduction of size of the main field of view as per the primary radiation admitting portion PA is negligible.

The wall elements is in the scatter radiation admitting portion SA may all be focused on the same location in space but preferably as is shown in FIG. 3 C) the scatter radiation admitting portion SA may include different segments wherein the respective wall elements are directed to different locations in space.

Although the grid structure GS in FIG. 3 are shown as "1D", "2D" grids are also envisaged herein. In 1D grids, the strips are arranged in one set along one direction whilst in 2D grids there are two sets of strips, one set of strips arranged along as first direction and the strips of the other set arranged in a second direction across the first direction to form a checkered pattern when viewed in plan view. The grid structure GS may be manufactured by sintering, for instance DMLS (direct metal laser sintering) or SLS (selective laser sintering).

It will be understood that the use of parts of the detector XD pixels for the sensors $SX_i$ by way of grating structure GS may be combined with the earlier embodiments described above where the one or more sensors are not part of the detector XD, eg are mounted elsewhere in the room RM or on the imager XI.

Figure 4:
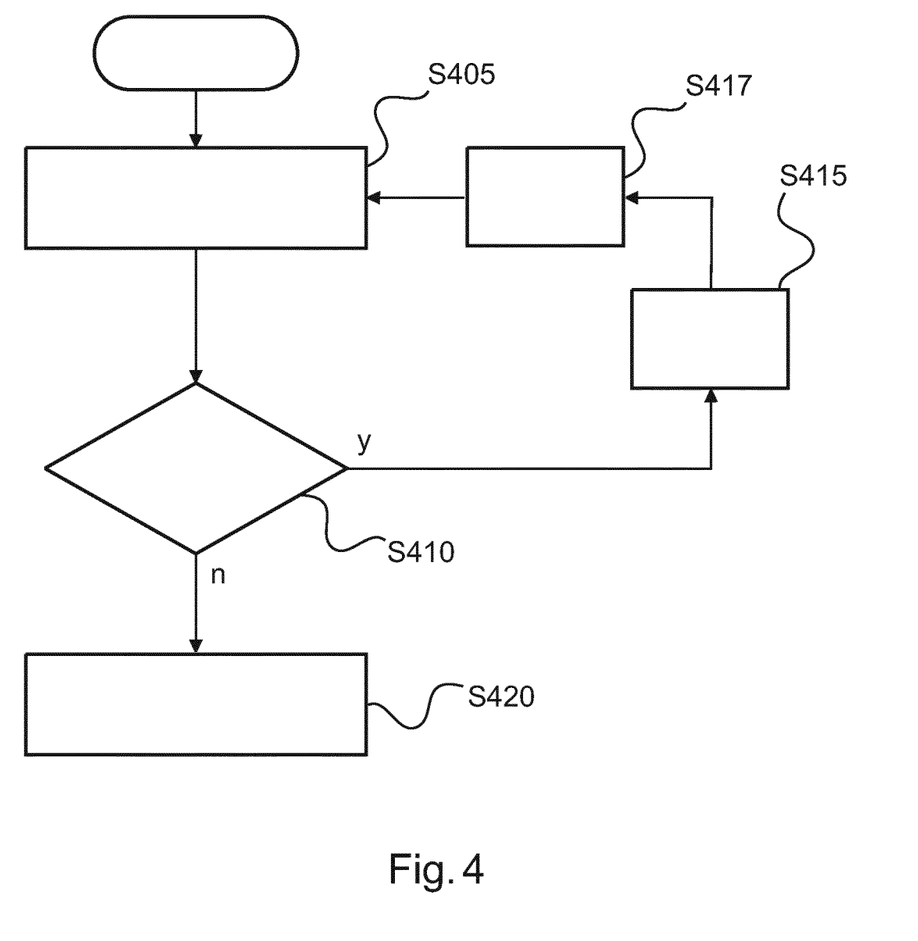
FIG. 4 is a flow chart of a method for supporting X-ray imaging.

Reference is now made to FIG. 4 where a method underlying operation of the previously described system in FIG. 1 is shown as a flow chart. It will be understood, however, that the method described below is not necessarily tied to the architecture as shown in FIG. 1. Specifically, the method may be understood as a teaching in its own right.

In step S405 one or more measurements of x-radiation scatter are received. The one or more measurements have been sensed by one or more sensors during operation of an X-ray source of an imager to expose a patient PAT to X-radiation. The scatter measurements may be acquired during an actual X-ray exposure for imaging or during a scout scan. The sensors may be of the indirect or direct conversion type. They may be distributed in the floor and/or ceiling and/or wall of the examination room. Preferably one or more of the sensors are arranged at an entrance of the room. In addition or instead, the sensors may be arranged in the imager, in particular on the X-ray source housing, the gantry, at the periphery of the detector. The sensors should be placed outside the volume floodable by the main radiation beam XB.

Preferably, the X-ray sensors are different from the X-ray detector of the imager. Preferably, more than one sensor is used, distributed around the imaging apparatus. In the alternative, one or more pixels of the X-ray detector itself may be used as the sensor. In this embodiment suitable directional elements is of a grid structure GS are superimposed on the X-ray detector to shield the said pixels from receiving primary radiation and to direct said pixels to receive only, or substantially only, scatter radiation.

Based on the said (preferably digitalized) scatter measurements, in step S410 a prediction is performed as to whether or not a second person P (other than the patient PAT) is present in the examination room during X-radiation exposure, in particular whether the second person is within too close a proximity ("danger zone") to the X-ray imager.

Instead of or in addition to detecting the presence of an additional person inside the room or in the danger zone, the received x-radiation may be used instead to predict whether the patient PAT has received or is receiving sufficient X-ray exposure. The first embodiment of the prediction step rests on the observation that the presence of an additional person in the room would increase the amount of scattered radiation. The second embodiment on sufficiency of exposure rests on the observation that the higher the body mass of the patient the higher the X-ray dosage is required in order to ensure a predefined image quality and that using the correct energy of x-radiation given the patient's body mass will result in a certain minimal amount of scatter and this can be ascertained based on the scatter measurements.

An outcome of the prediction is then output at step S415 in form of a prediction signal. If the predictor signal indicates that no additional person is present and/or that exposure is sufficient, imaging may commence or continue. In particular, and acceding to one embodiment, the user may switch from scout imaging to actual imaging if no presence of the additional person was predicted.

Alternatively, if the prediction signal indicates that the additional person is present during exposure or that the present exposure is not sufficient, different actions may be taken at step S417. Actions envisaged herein include to effect driving a transducer to produce an alert signal to issue an invitation to the user to re-try the imaging session after having the additional person in the room removed or have the additional person moved further away from the X-ray source, or similar. Other actions in step S417 include shutting down or locking down or to otherwise disable the X-ray imaging apparatus, in particular the X-ray source, to prevent (further) misuse. In addition or instead, the actions performed at step S417 may include a re-collimation of the X-ray beam of the X-ray source and/or may include displaying on a screen the correct voltage to be used for the given patient, that is the voltage where the dose on patient PAT is low (eg, lowest possible) whilst a pre-set image quality is maintained for the region of interest one wishes to image. The re-collimation may help reduce dose exposure.

If the predictor signal indicates that there is insufficient exposure, a suitable action at times may require to actually increase the dose (eg, by increasing the tube voltage or time etc.) to ensure the required image quality can be achieved.

Steps S405, S410 may be repeated in a loop at a suitable sampling frequency to process a stream of scatter measurements. In this manner, the method is able to establish whether the additional person has been removed in the meantime or that the exposure is now sufficient, in which case imaging can continue or resume at step S420 whilst the preventive actions cease.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An imaging system, comprising:
    an X-ray imager;
    at least one X-ray sensor;
    an input interface for receiving an X-radiation scatter obtained by the at least one X-ray sensor during operation of the X-ray imager for imaging a first object;
    a processor configured to predict, based on the scatter, whether a second, not imaged, object is present in an examination room, wherein the at least one X-ray sensor is arranged away from the second object and configured to detect an additional scatter which is above a normal scatter to be expected if the second object is not present in the examination room other than the first object, or there is sufficient X-ray exposure of the first object if the normal scatter to be expected for the first object having a known mass is detected by the at least one X-ray sensor; and
    an output interface for outputting a predictor signal indicative of an outcome of said prediction.

2. The imaging system according to claim 1, further comprising a transducer configured to issue an alert signal in response to the predictor signal, said transducer being at least one of auditory and optical.

3. The imaging system according to claim 1, further comprising displaying on a display a message in relation to the predictor signal.

4. The imaging system according to claim 1, wherein a message in relation to said predictor signal is transmitted over a communication network to a recipient.

5. The imaging system according to claim 1, wherein an action is caused to affect the dose of X-radiation received at the first object based on the predictor signal.

6. The imaging system according to claim 1, wherein the X-ray imager comprises an X-ray detector for imaging the first object, and where the at least one sensor is different from said X-ray detector.

7. The imaging system according to claim 1, wherein the X-ray imager comprises an X-ray detector, wherein the at least one sensor is part of the X-ray detector.

8. The imaging system according to claim 1, wherein operation of the processor is based on a machine learning algorithm trained by one or more samples of X-radiation scatter measurements.

9. The imaging system according to claim 1, wherein the processor is configured to compare the scatter against one or more pre-defined X-radiation scatter thresholds.

10. The imaging system according to claim 1, wherein the X-ray imager is located in a room with the at least one X-ray sensor arranged on at least one of a wall, a floor, and a ceiling of said room.

11. The imaging system according to claim 1, wherein the at least one X-ray sensor is located on the X-ray imager.

12. A method of supporting X-ray imaging, comprising:
receiving an X-radiation scatter obtained by at least one X-ray sensor during operation of an X-ray source of an X-ray imager to expose a first object to X-radiation for imaging;
making a prediction, based on the scatter, whether a second, not imaged, object is present in an examination room, wherein the at least one X-ray sensor is arranged away from the second object and configured to detect an additional scatter which is above a normal scatter to be expected if the second object is not present in the examination room other than the first object, or there is sufficient X-ray exposure of the first object if the normal scatter to be expected for the first object having a known mass is detected by the at least one X-ray sensor; and
outputting a predictor signal indicative of an outcome of said prediction.

13. A non-transitory computer-readable medium having one or more executable instructions stored thereon which, when executed by at least one processor, cause the at least one processor to perform a method for supporting X-ray imaging, the method comprising:
receiving an X-radiation scatter obtained by at least one X-ray sensor during operation of an X-ray source of an X-ray imager to expose a first object to X-radiation for imaging;
making a prediction, based on the scatter, whether a second, not imaged, object is present in an examination room, wherein the at least one X-ray sensor is arranged away from the second object and configured to detect an additional scatter which is above a normal scatter to be expected if the second object is not present in the examination room other than the first object, or there is sufficient X-ray exposure of the first object if the normal scatter to be expected for the first object having a known mass is detected by the at least one X-ray sensor; and
outputting a predictor signal indicative of an outcome of said prediction.

\* \* \* \* \*